US009404894B2

(12) United States Patent
Tian

(10) Patent No.: US 9,404,894 B2
(45) Date of Patent: Aug. 2, 2016

(54) STANDING WAVE AMPLIFICATION DEVICE FOR VIBRATION SIGNAL COLLECTION AND LADLE SLAG VIBRATION SIGNAL DETECTION METHOD

(75) Inventor: Lu Tian, Hunan (CN)

(73) Assignee: HUNAN RAMON SCIENCE & TECHNOLOGY CO., LTD., Hunan (CN)

( * ) Notice: Subject to any disclaimer, the term of this patent is extended or adjusted under 35 U.S.C. 154(b) by 367 days.

(21) Appl. No.: 14/116,266

(22) PCT Filed: Jun. 28, 2011

(86) PCT No.: PCT/CN2011/076497
§ 371 (c)(1),
(2), (4) Date: Nov. 7, 2013

(87) PCT Pub. No.: WO2012/151778
PCT Pub. Date: Nov. 15, 2012

(65) Prior Publication Data
US 2014/0102203 A1 Apr. 17, 2014

(30) Foreign Application Priority Data

May 10, 2011 (CN) .......................... 2011 1 0120189

(51) Int. Cl.
*G01N 33/20* (2006.01)
*G01N 29/12* (2006.01)
*B22D 11/18* (2006.01)

(52) U.S. Cl.
CPC .............. *G01N 29/12* (2013.01); *B22D 11/186* (2013.01); *G01N 33/20* (2013.01)

(58) Field of Classification Search
USPC ............................ 73/649, 617, 644, 587, 579
See application file for complete search history.

(56) References Cited

U.S. PATENT DOCUMENTS

| 5,042,700 A * | 8/1991 | Ardell et al. .................. 222/590 |
| 6,737,014 B2 * | 5/2004 | Davidkhanian et al. ........ 266/45 |
| 2001/0029785 A1 * | 10/2001 | Heaslip et al. .................. 73/579 |

FOREIGN PATENT DOCUMENTS

| CN | 1926412 A | 3/2007 |
| CN | 201505712 U | 6/2010 |

(Continued)

OTHER PUBLICATIONS

International Search Report for PCT/CN2011/076497 Feb. 16, 2012.

*Primary Examiner* — Hezron E Williams
*Assistant Examiner* — Xin Zhong
(74) *Attorney, Agent, or Firm* — Pearne & Gordon LLP

(57) ABSTRACT

A standing wave amplification device for vibration signal collection includes a sensing rod (11) acting as standing wave transmission medium. A standing wave formation device includes two fixing support devices (12) distributed along the axial direction and connecting the sensing rod (11) to an operating arm (14). The two fixing support devices (12) respectively collect vibration waves and transmit them to the sensing rod (11) from two different locations of the operating arm (14). The vibration waves are superimposed to form a standing wave on the sensing rod (11). A vibration sensor (13) is connected to the sensing rod (11) and the vibration sensor (13) is between the two fixing support devices (12). A wave detected by the vibration sensor (13) is the standing wave. Compared with transverse wave or longitudinal wave transmitted in the transmission medium of prior art, the standing wave has advantages of larger amplitude and more obvious vibration effect. A ladle slag vibration signal detection method based on the device also has said advantages. The sensing rod (11) can make physical resonance, by which the standing wave signal is amplified and real warning rate of ladle slag is improved effectively.

16 Claims, 5 Drawing Sheets

(56) References Cited

FOREIGN PATENT DOCUMENTS

| | | |
|---|---|---|
| CN | 101774000 A | 7/2010 |
| CN | 101905302 A | 12/2010 |
| CN | 101987351 A | 3/2011 |
| CN | 202087805 U | 5/2011 |
| JP | 2006281218 A | 10/2006 |

* cited by examiner

STANDING WAVE AMPLIFICATION DEVICE FOR VIBRATION SIGNAL COLLECTION AND LADLE SLAG VIBRATION SIGNAL DETECTION METHOD

The present application is the national phase of International Application No. PCT/CN2011/076497 filed on Jun. 28, 2011, which claims the benefit of priority to Chinese patent application No. 201110120189.4 titled "STANDING WAVE AMPLIFICATION DEVICE FOR VIBRATION SIGNAL COLLECTION AND LADLE SLAG VIBRATION SIGNAL DETECTION METHOD", filed with the Chinese State Intellectual Property Office on May 10, 2011. The entire disclosure of the application is incorporated herein by reference.

FIELD OF THE INVENTION

The present application relates to the field of metallurgical industry, and in particular to a standing wave amplification device for vibration signal acquisition and a ladle slag vibration signal detection method.

BACKGROUND OF THE INVENTION

From the founding of the People's Republic of China to now, after many years of construction and development, China's iron and steel industry has made significant achievements; and meanwhile, the market also imposes increasingly high requirements on quality for the iron and steel industry.

In the continuous casting industry, at the end of casting of a ladle of molten steel, slag floating on the molten steel in the ladle will gradually flow into the tundish. Excessive tundish slag degrades purity of the molten steel, speeds up erosion of the tundish lining, and influences quality of a billet. Thus, it is necessary to control the flowing of the slag from the ladle to the tundish, which is very important for improving the quality of the billet.

In recent years, the technology of reflecting a state of ladle slag by detecting vibration signals of molten steel with slag becomes prevalent internationally.

Reference is made to FIG. 1, which is a structural schematic view of a ladle slag vibration signal detection device in the prior art.

Molten steel in a ladle 01 flows into a tundish 02 via a shroud protective tube 03 to which an operating arm 04 is connected. A vibration signal detection device includes a telescopic pipe 06 and a vibration sensor (not shown) mounted inside a fixing casing 05. The telescopic pipe 06 has a telescopic function, with its telescopic end optionally abutting against the shroud protective tube 03, and its fixed end being connected with the vibration sensor mounted inside the casing 05. When the telescopic end of the telescopic pipe 06 abuts against the shroud protective tube 03, the telescopic pipe 06 serves as a vibration transmission medium to transmit a vibration signal to the vibration sensor at the other end. Since the different proportion of the steel slag to the molten steel causes the different vibration signal of flowing impact, by detecting the variations of this signal, the vibration signal detection device may determine a state of the ladle slag, and further control the slag flowing down from the ladle.

However, in the above ladle slag detection device, only the telescopic end of the telescopic pipe 06 contacts with the vibration source, while the other end transmits vibration wave signals to the vibration sensor. The vibration waves may only be transmitted in one direction from the telescopic end of the telescopic pipe 06 to the vibration sensor at the fixed end of the telescopic pipe 06, and the waves received by the vibration sensor are transverse waves or longitudinal waves with weak vibration signals, thus affecting the true alarm rate of the ladle slag.

Therefore, it is an important technical problem to be solved by those skilled in the art to improve the true alarm rate of a ladle slag.

SUMMARY OF THE INVENTION

To solve the above technical problem, there is provided in the present application a standing wave amplification device for vibration signal acquisition, which is capable of improving a true alarm rate effectively as compared with a ladle slag vibration signal detection device in the prior art. There is further provided in the present application a ladle slag vibration signal detection method based on the above standing wave amplification device for vibration signal acquisition.

A standing wave amplification device for vibration signal acquisition according to the present application includes:
 a sensing rod serving as a standing wave propagation medium;
 a standing wave forming means, including two fixing support means distributed axially and connecting the sensing rod to an operating arm, wherein the two fixing support means acquire vibration waves respectively from two different positions on the operating arm, and transmit the acquired vibration waves to the sensing rod, the vibration waves transmitted are superimposed on the sensing rod to form a standing wave; and
 a vibration sensor connected to the sensing rod, wherein the vibration sensor is located between the two fixing support means, and detects the standing wave.

Preferably, the sensing rod is an elastic solid sensing rod.

Preferably, the two fixing support means are connected to the operating arm and the sensing rod in such a manner that the relative position between the two fixing support means is adjustable.

Preferably, each of the two fixing support means includes:
 a U-shaped fastener provided on an outer circumferential surface of the operating arm, and having two ends each provided with a thread;
 a fixing plate provided with two through holes through which the two ends of the "U"-shaped fastener pass respectively, wherein the fixing plate is connected with the "U"-shaped fastener by preload nuts engaged with the threads of the "U"-shaped fastener; and
 a clamp connected to the fixing plate, wherein the sensing rod is clamped inside the clamp, and a side wall of the clamp is provided with a threaded hole through which a bolt abuts against the sensing rod.

Preferably, an outer circumferential surface of the sensing rod is marked with scales.

Preferably, the vibration sensor is connected to the sensing rod by a fixing seat.

Preferably, the fixing seat includes a base and a fixing member configured to fix the base to the sensing rod, and the vibration sensor is connected to the base.

Preferably, the vibration sensor is mounted in a shielding protection box connected to the base by socket-head cap screws.

A ladle slag vibration signal detection method based on any one of the standing wave amplification devices for vibration signal acquisition described above is further provided in the present application, including:
 1) acquiring vibration waves at any two points on the operating arm by the two fixing support means, and superimposing, on the sensing rod, the vibration waves at the any two points so as to form a standing wave, wherein a natural frequency of the sensing rod becomes the same as the frequency of the standing wave, thus achieving resonance of the sensing rod and amplifying the standing wave; and 2) acquiring, by the vibration sensor, the standing wave amplified and determining whether to initiate an alarm.

A standing wave amplification device for vibration signal acquisition according to the present application includes a sensing rod, a standing wave forming means and a vibration sensor. The sensing rod serves as a standing wave propagation medium. The standing forming means includes two fixing support means by which the sensing rod is fixed to an operating arm. Vibration waves are propagated to the sensing rod by the two fixing support means and are superimposed on the sensing rod between the two fixing support means so as to form a standing wave for being propagated. Compared with waves on a propagation medium in the prior art being transverse waves or longitudinal waves, this application is advantageous in that the wave propagated on the sensing rod is a standing wave with a larger wave amplitude and the significant vibration effect. Also, the vibration sensor detects only the standing wave without being affected by the transverse waves or longitudinal waves in the surrounding environment, and thus interference signals may be filtered out. Furthermore, in the standing wave amplification device for vibration signal acquisition according to the present application, by setting a distance between the fixing support means at two sides of the vibration sensor, the natural frequency of the sensing rod between the two fixing support means becomes the same as the vibration frequency of the above standing wave, thereby inducing a physical resonance of the sensing rod between the two fixing support means. Thus, the vibration signal received by the vibration sensor is strong, which effectively improves the true alarm rate of the ladle slag.

In addition, in the standing wave amplification device for vibration signal acquisition according to this application, since the sensing rod is fixed to the operating arm by the two fixing support means, a segment of the sensing rod between the two fixing support means can receive vibration weaves transmitted only by the two fixing support means, that is, this segment of the sensing rod vibrates only with the vibration of the operating arm without being interfered by other external vibrations. Therefore, the standing wave amplification device for vibration signal acquisition according to this embodiment has a stronger anti-interference capability, and improves the true alarm rate.

In a preferred solution according to the present application, the two fixing support means are connected to the operating arm and the sensing rod in such a manner that the relative position between the two fixing support means is adjustable. It should be noted that, due to differences between continuous casting environments, frequencies of the vibration waves during the ladle slag will be different as well. In the standing wave amplification device for vibration signal acquisition according to the present application, by adjusting the relative position between the fixing support means, the natural frequency of the sensing rod between the two fixing support means becomes the same as the vibration frequency of a standing wave propagated on the sensing rod, thereby achieving physical resonance of the sensing rod between the two fixing support means. Thus, the standing wave amplification device for vibration signal acquisition according to the present application can be applicable to different production sites.

A ladle slag vibration signal detection method based on any one of the standing wave amplification devices for vibration signal acquisition described above according to the present application includes:

1) acquiring vibration waves at any two points on the operating arm by the two fixing support means, and superimposing, on the sensing rod, the vibration waves at the any two points so as to form a standing wave, wherein a natural frequency of the sensing rod becomes the same as the frequency of the standing wave, thus achieving resonance of the sensing rod and amplifying the standing wave; and 2) acquiring, by the vibration sensor, the standing wave amplified and determining whether to initiate an alarm.

Thus the real alarm rate of the ladle slag is improved.

DETAILED DESCRIPTION OF THE EMBODIMENTS

An object of the present application is to provide a standing wave amplification device for vibration signal acquisition which has a higher true alarm rate. Another object of the present application is to provide a ladle slag vibration signal detection method based on the device.

Technical solutions in embodiments of the present application will be described clearly and completely hereinafter in conjunction with the drawings in the embodiments of the present application. Apparently, the described embodiments are only a part of the embodiments of the present application, not all embodiments. Based on the embodiments in the present application, all of other embodiments, made by the person skilled in the art without any creative efforts, fall into the protection scope of the present application.

Figure 1:
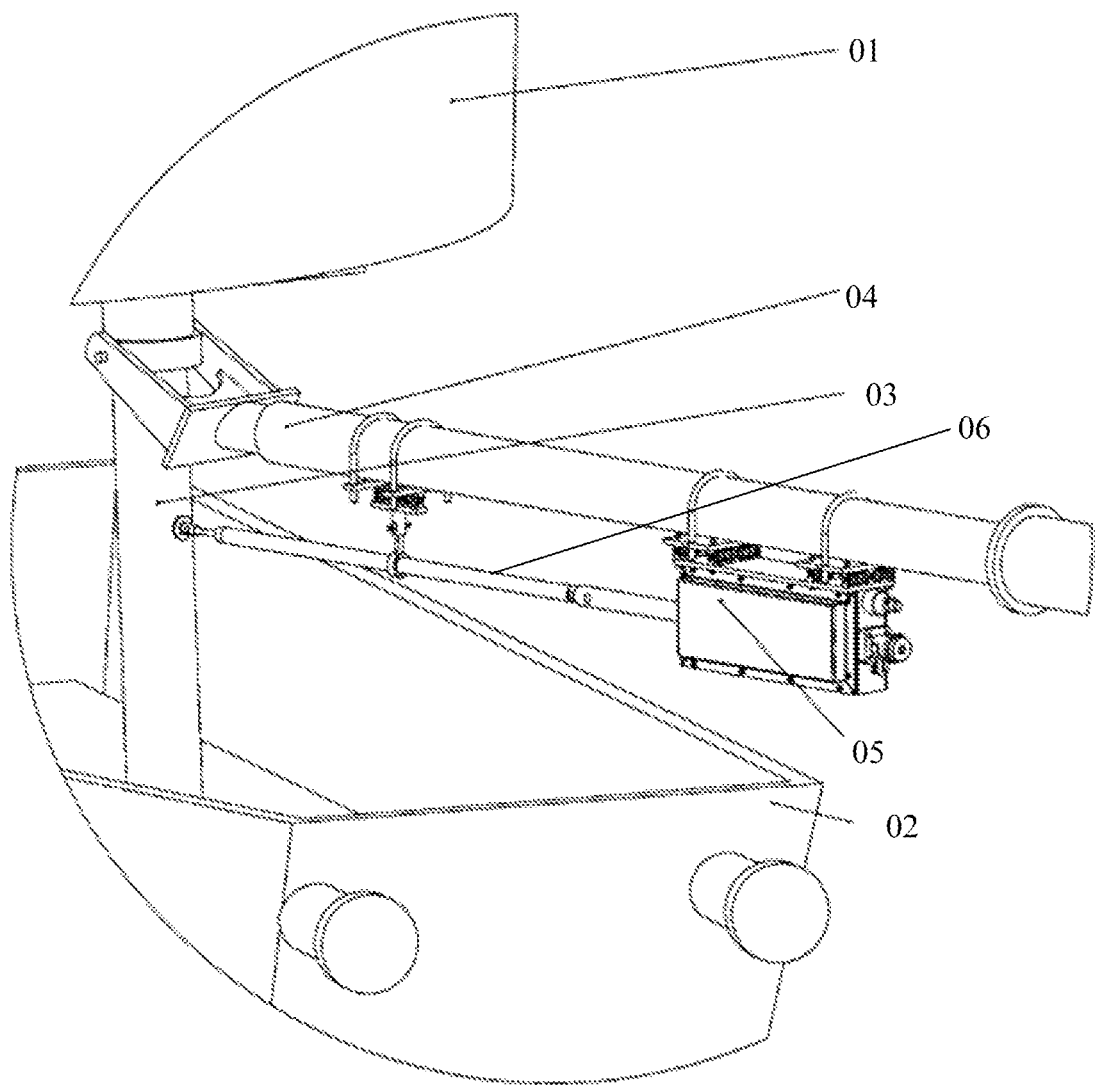
FIG. 1 is a schematic structural view of a ladle slag vibration signal detection device in the prior art.
Figure 2:
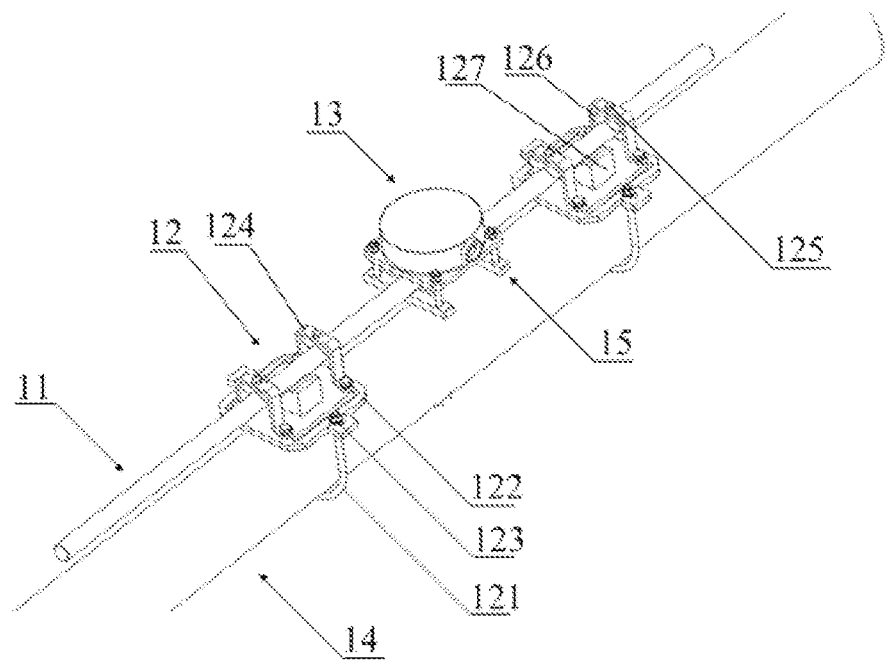
FIG. 2 is a schematic structural view of a standing wave amplification device for vibration signal acquisition according to a first embodiment of the present application.

Reference is made to FIG. 2, which is a schematic structural view of a standing wave amplification device for vibration signal acquisition according to an embodiment of the present application.

A standing wave amplification device for vibration signal acquisition according to this embodiment includes a sensing rod 11, two fixing support means 12 and a vibration sensor 13. Specifically, the sensing rod 11 is mounted to an operating arm 14 by the two fixing support means 12. The vibration sensor 13 is connected to the sensing rod 11 between the two fixing support means 12.

It should be noted that, the ladle slag process may cause vibration of the operating arm 14. Since the sensing rod 11 is connected to the operating arm 14 by the two fixing support means 12, vibration waves on the operating arm 14 may be transmitted to the sensing rod 11 via the two fixing support means 12 and superimposed to form a standing wave. Further, the sensing rod 11, as standing wave transmission medium, transmits the standing wave to the vibration sensor 13.

With such configuration, in the standing wave amplification device for vibration signal acquisition according to this embodiment, vibration waves generated by the operating arm are transmitted via the two fixing support means to the sensing rod between the two fixing support means in different directions and are superimposed to form a standing wave. Compared with waves on a propagation medium in the prior art being transverse waves or longitudinal waves, this embodiment is advantageous in that the wave propagated on the sensing rod is a standing wave with a larger wave amplitude and the significant vibration effect. Also, the vibration sensor detects only the standing wave without being affected by the transverse waves or longitudinal waves in the surrounding environment, and thus interference signals may be filtered out. Furthermore, in the standing wave amplification device for vibration signal acquisition according to the present application, by setting a distance between the fixing support means 12 at two sides of the vibration sensor, the natural frequency of the sensing rod 11 between the two fixing support means 12 becomes the same as the vibration frequency of the above standing wave, thereby inducing a physical resonance of the sensing rod 11 between the two fixing support means 12. Thus, the vibration signal received by the vibration sensor 13 is strong, which effectively improves the true alarm rate of the ladle slag.

In addition, in the standing wave amplification device for vibration signal acquisition according to this embodiment, since the sensing rod 11 is fixed to the operating arm 14 by the two fixing support means 12, a segment of the sensing rod 11 between the two fixing support means 12 can receive vibration weaves transmitted only by the two fixing support means 12, that is, this segment of the sensing rod 11 vibrates only with the vibration of the operating arm 14 without being interfered by other external vibrations. Therefore, the standing wave amplification device for vibration signal acquisition according to this embodiment has a stronger anti-interference capability, which apparently improves the true alarm rate.

Since production environments in various steel plants are different one from another, frequencies of vibration waves in different production sites differ from each other. In order that the standing wave amplifying device for vibration signal acquisition according to the present application can be applicable to different production site environments, in a preferred embodiment of the present application, the two fixing support means 12 are connected to the operating arm 14 and the sensing rod 11 in such a manner that the relative position between the two fixing support means 12 is adjustable.

It should be noted that, the expression that "the relative position between the two fixing support means 12 is adjustable" means that positions of the two fixing support means 12 are adjustable in an axial direction of the operating arm 14. As such, when the vibration frequency of the operating arm 14 is changed during the ladle slag process at a production site, by adjusting the relative position between the two fixing support means 12, the natural frequency of the sensing rod 11 between the two fixing support means 12 becomes the same as the vibration frequency of a standing wave propagated on the sensing rod 11, thereby achieving physical resonance of the sensing rod 11. Thus, the standing wave amplification device for vibration signal acquisition according to this embodiment can be applicable to various production environments.

The relative position between the above two fixing support means 12 may be adjusted by various means, for example, by the following configuration.

Figure 3:
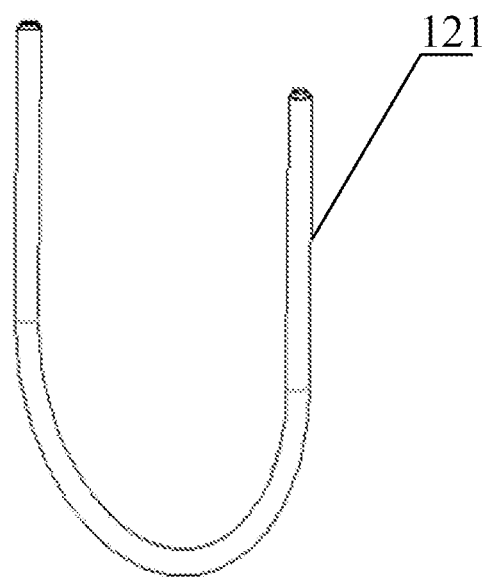
FIG. 3 is a schematic structural view of a "U"-shaped fastener according to an embodiment of the present application.
Figure 4:
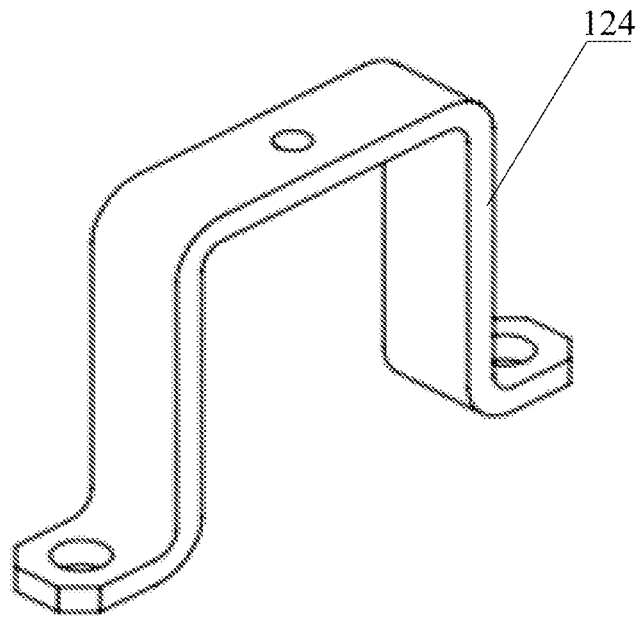
FIG. 4 is a schematic structural view of a clamp according to an embodiment of the present application.
Figure 5:
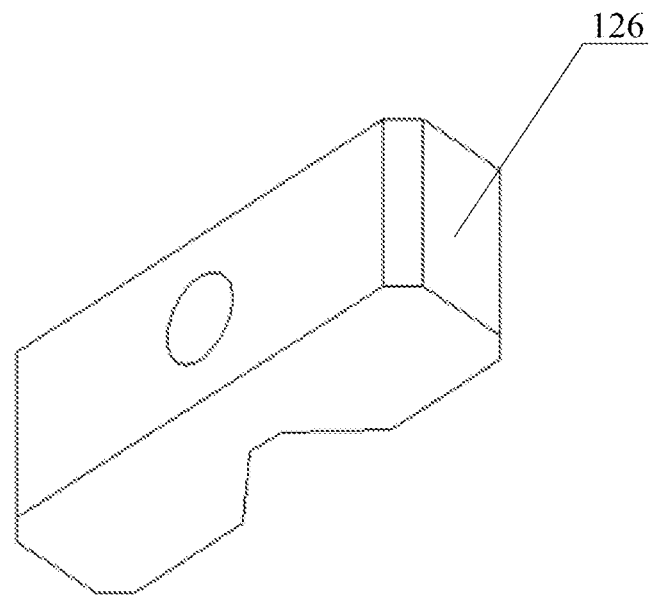
FIG. 5 is a schematic structural view of a seat pad according to an embodiment of the present application.

Reference is made to FIGS. 3 to 5. FIG. 3 is a schematic structural view of a "U"-shaped fastener according to an embodiment of the present application; FIG. 4 is a schematic structural view of a clamp according to an embodiment of the present application; and FIG. 5 is a schematic structural view of a seat pad according to an embodiment of the present application.

Each of the two fixing support means 12 according to this embodiment may include a "U"-shaped fastener 121, and each of the two ends of the "U"-shaped fastener 121 is provided with a thread (not shown). It should be noted that, the "U" shape here refers to a shape capable of tightly surrounding the operating arm 14 when the operating arm 14 is circular. Apparently, when the operating arm 14 has a cross section in any other shape, the fastener may also be in any other corresponding shape. For example, when the cross section of the operating arm 14 is in a square shape, the fastener may also be correspondingly in a square shape.

Each of the above two fixing support means 12 further includes a fixing plate 122 provided with two through holes through which the two ends of the "U"-shaped fastener 121 pass respectively. The fixing plate 122 is connected with the "U"-shaped fastener 121 by a preload nut 123 engaged with the thread of the "U"-shaped fastener 121. As such, an enclosure structure defined by the fixing plate 122 and the "U"-shaped fastener 121 may clamp the outer circumferential surface of the operating arm 14.

Each of the two fixing support means 12 according to this embodiment further includes a clamp 124 connected to the fixing plate 122. The sensing rod 11 is clamped inside the clamp 124. A side wall of the clamp 124 is provided with a threaded hole through which a bolt 125 abuts against the sensing rod 11. Apparently, in order to enable the sensing rod 11 to be more stably clamped inside the clamp 124, each of the two fixing support means 12 according to this embodiment may further include a seat pad 126 and a spacer 127. The seat pad 126 is provided with a recess matched with the outer circumferential surface of the sensing rod 11. Apparently, the spacer 127 also needs to be provided with a recess matched with the outer circumferential surface of the sensing rod 11. The seat pad 126 is compressed inside the clamp 124 and on the sensing rod 11, and the spacer 127 is padded at a side of the sensing rod 11 opposite to the seat pad 126. In such configuration, with the seat pad 126 and the spacer 127, the clamp 124 may fix the sensing rod 11 to the fixing plate 122 more stably.

With such configuration, when the standing wave amplification device for vibration signal acquisition according to this embodiment is applied to a different production site, the positions of the two fixing support means 12 are required to be adjusted. The preload nut 123 may be unscrewed, therefore enabling the looseness between the "U"-shaped fastener and the operating arm 14. Then, the bolt 125 may be unscrewed, so as to enable the looseness between the clamp 124 and the sensing rod 11. In this way, the positions of the two fixing support means 12 may be adjusted. After the completion of the adjustment, the nut 123 and the bolt 125 are screwed tightly. Thus, the sensing rod 11 can be fixed and the relative position between the two fixing support means 12 can be adjusted effectively.

Apparently, in order to more conveniently adjust the relative position between the two fixing support means 12, the outer circumferential surface of the sensing rod 11 is marked with scales, and the unit length of the scale may be determined depending on specific conditions. As such, in the standing wave amplification device for vibration signal acquisition according to this embodiment, the positions of the fixing support means 12 may be adjusted specifically with reference to the scales on the sensing rod 11. Apparently, such a configuration further improves convenience of adjusting the fixing support means 12.

Figure 6:
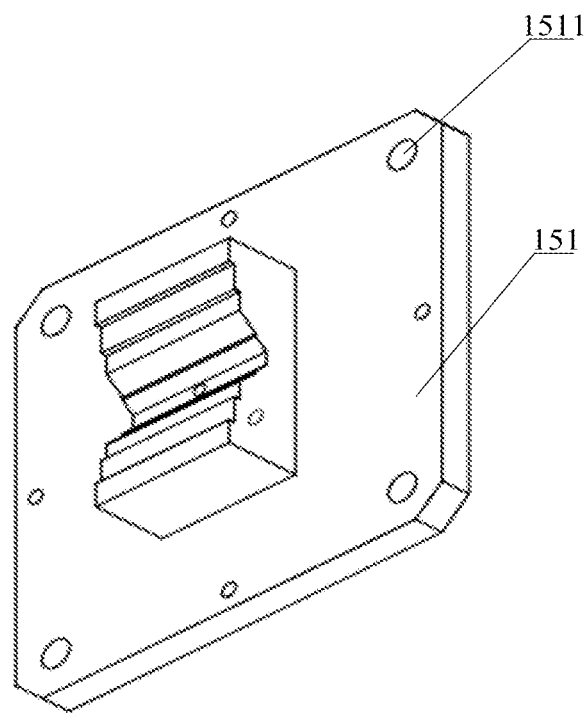
FIG. 6 is a schematic structural view of a base according to an embodiment of the present application.
Figure 7:
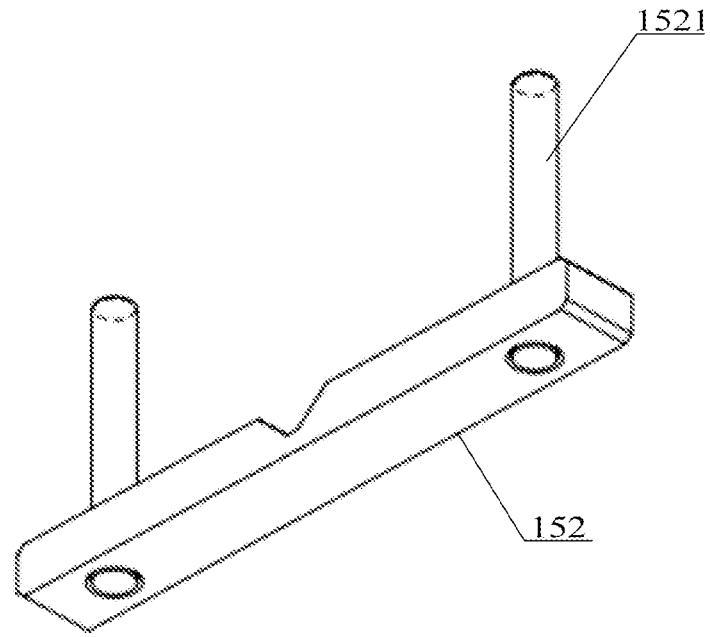
FIG. 7 is a schematic structural view of a fixing member according to an embodiment of the present application.

Reference is made to FIGS. 6 and 7. FIG. 6 is a schematic structural view of a base according to an embodiment of the present application; and FIG. 7 is a schematic structural view of a fixing member according to an embodiment of the present application.

In addition, in the standing wave amplification device for vibration signal acquisition according to this embodiment, the vibration sensor 13 can be connected to the sensing rod 11 by a fixing seat 15. Apparently, the vibration sensor 13 may also be connected to the sensing rod 11 directly. The fixing seat 15 may include a base 151 and a fixing member 152 configured to fix the base 151 to the sensing rod 11, which will be described below. The base 151 is provided with a plurality of through holes 1511, and the fixing member 152 is provided with supporting legs 1521 whose end is provided with a thread. The segment of the supporting leg 1521 provided with the thread may pass through the through hole 1511, and together with a nut engaged with the thread, connects the fixing member 152 and the base 151. As such, the sensing rod 11 may be clamped between the fixing member 152 and the base 151. The base 151 is configured for mounting the vibration sensor 13.

Figure 8:
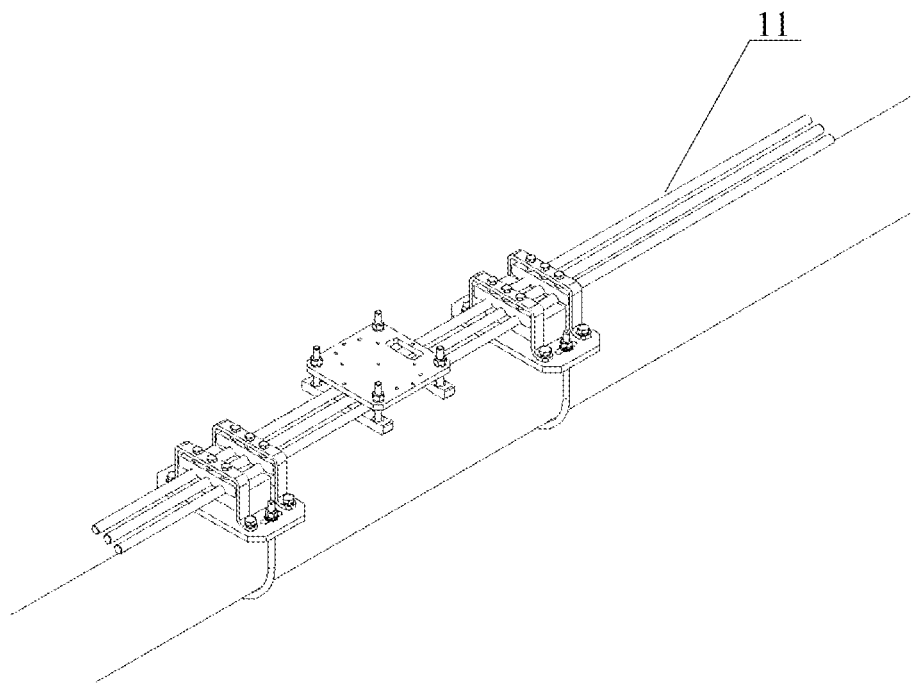
FIG. 8 is a schematic structural view of a standing wave amplification device for vibration signal acquisition according to a second embodiment of the present application.

Reference is made to FIG. 8, which is a schematic structural view of a standing wave amplification device for vibration signal acquisition according to another embodiment of the present application.

Apparently, in order to improve the intensity of the vibration wave received by the vibration sensor 13, the standing wave amplification device for vibration signal acquisition according to this embodiment may be provided with a plurality of sensing rods 11 each connected to the vibration sensor 13 by the fixing seat 15. With such configuration, in the standing wave amplification device for vibration signal acquisition according to this embodiment, vibration waves received by the vibration sensor 13 are provided from the plurality of sensing rods 11, having an greater intensity than that from a single sensing rod 11. Thus, with such configuration, the true alarm rate of the standing wave amplification device for vibration signal acquisition may be further improved.

In addition, in the standing wave amplification device for vibration signal acquisition according to this embodiment, the sensing rod 11 is a solid sensing rod. It should be noted that, in case of the same vibration intensity of the vibration source, vibration intensity sensed by a solid sensing rod is greater than that by a hollow sensing rod. Also, the solid sensing rod is desired to have certain elasticity, in order to transmit the vibration waves generated by the operating arm 14 with a higher sensitivity. The sensing rod may specifically be a solid copper rod, or may also be of any other material such as an aluminum, magnesium, copper, zinc, etc.

Figure 9:
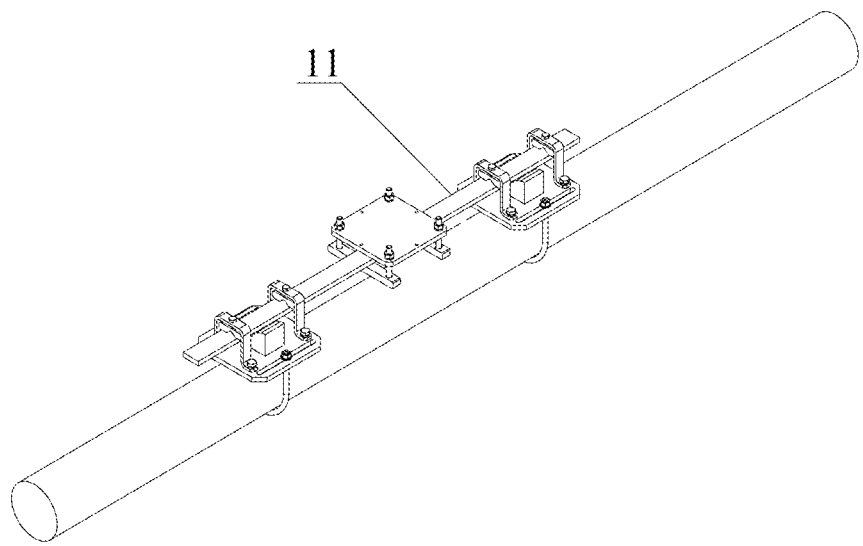
FIGS. 9 is a schematic structural view of a standing wave amplification device for vibration signal acquisition according to an embodiment of the present application with a sensing rod being a lath-shaped solid rod.

In addition, the sensing rod 11 may specifically be of a lath-shaped solid rod. Reference is made to FIG. 9, which is a schematic structural view of a standing wave amplification device for vibration signal acquisition according to an embodiment of the present application with a sensing rod being a lath-shaped solid rod.

As such, vibration waves at two points on the operating arm are acquired by the two fixing support means, and are transmitted to the lath-shaped solid rod, and are superimposed to form a standing wave. The vibration frequency of molten steel in a ladle shroud is made to be the same as the frequency of the standing wave, thus achieving resonance, and amplifying the standing wave.

Apparently, the sensing rod may also be of a cylindrical structure, or may be of any other structure, such as a cup-shaped solid rod, a curved solid rod, various irregular-shaped solid body, etc. Specifically, the shape and material of the sensing rod are not limited in the present application.

It should be noted that, due to a harsh environment of the production site, the vibration sensor 13 is vulnerable. Thus, in the standing wave amplification device for vibration signal acquisition according to this embodiment, the vibration sensor 13 may be mounted in a shielding protection box which can be mounted to the base 151 by screws. With such configuration, in the standing wave amplification device for vibration signal acquisition according to this embodiment, it is possible to effectively prevent dust in the production site from entering into the interior of the vibration sensor 13, and may further prevent damage to the vibration sensor 13.

In addition, since the cold air, when performing a cooling process to the vibration sensor 13, may generate noises due to contact with the above screws, the noises may induce vibration and the induced vibration may in turn adversely affect the real alarm rate of the ladle slag. In view of the problem, socket-head cap screws may be employed as the above screws. With such configuration, the screws do not have to be exposed to the outside of the shielding protection box, thus avoiding generation of noises effectively.

There is further provided in this embodiment a ladle slag vibration signal detection method based on a standing wave amplification device for vibration signal acquisition in any one of the above embodiments, and the method includes:

1) acquiring vibration waves at any two points on the operating arm by the two fixing support means, and superimposing the vibration waves at the any two points on the sensing rod so as to form a standing wave, wherein the natural frequency of the sensing rod is made to be the same as the frequency of the standing wave, thus achieving resonance of the sensing rod, and amplifying the standing wave; and 2) collecting the amplified standing wave by a vibration sensor acquires, and determining whether to initiate an alarm.

Thus, the real alarm rate of the ladle slag is improved.

A standing wave amplification device for vibration signal acquisition and a ladle slag vibration signal detection method based on the device according to the present application have been described in detail hereinbefore. The principle and implementation of the present application are illustrated herein by specific examples. The above description of examples is only intended to help understanding the method and the spirit of the present application. It should be noted that, for the person skilled in the art, many modifications and improvements may be made to the present application without departing from the principle of the present application, and these modifications and improvements are also deemed to fall into the protection scope of the present application defined by the claims.

What is claimed is:

1. A standing wave amplification device for vibration signal acquisition, comprising:
   a sensing rod serving as a standing wave propagation medium;
   a standing wave forming means, comprising two fixing support means distributed axially and connecting the sensing rod to an operating arm, wherein the two fixing support means acquire vibration waves respectively from two different positions on the operating arm, and transmit the acquired vibration waves to the sensing rod, the vibration waves transmitted are superimposed on the sensing rod to form a standing wave; and
   a vibration sensor connected to the sensing rod, wherein the vibration sensor is located between the two fixing support means, and detects the standing wave.

2. A ladle slag vibration signal detection method based on the standing wave amplification device for vibration signal acquisition according to claim 1, comprising:
   1) acquiring vibration waves at any two points on the operating arm by the two fixing support means, and superimposing, on the sensing rod, the vibration waves at the any two points so as to form a standing wave, wherein a vibration frequency of molten steel in a ladle shroud becomes the same as a frequency of the standing wave, thus achieving resonance and amplifying the standing wave; and
   2) acquiring, by the vibration sensor, the standing wave amplified and determining whether to initiate an alarm.

3. The standing wave amplification device for vibration signal acquisition according to claim 1, wherein the sensing rod is an elastic solid sensing rod.

4. A ladle slag vibration signal detection method based on the standing wave amplification device for vibration signal acquisition according to claim 3, the method comprising:
   1) acquiring vibration waves at any two points on the operating arm by the two fixing support means, and superimposing, on the sensing rod, the vibration waves at the any two points so as to form a standing wave, wherein a vibration frequency of molten steel in a ladle shroud becomes the same as a frequency of the standing wave, thus achieving resonance and amplifying the standing wave; and
   2) acquiring, by the vibration sensor, the standing wave amplified and determining whether to initiate an alarm.

5. The standing wave amplification device for vibration signal acquisition according to claim 3, wherein the two fixing support means are connected to the operating arm and the sensing rod in such a manner that the relative position between the two fixing support means is adjustable.

6. A ladle slag vibration signal detection method based on the standing wave amplification device for vibration signal acquisition according to claim 5, comprising:
   1) acquiring vibration waves at any two points on the operating arm by the two fixing support means, and superimposing, on the sensing rod, the vibration waves at the any two points so as to form a standing wave, wherein a vibration frequency of molten steel in a ladle shroud becomes the same as a frequency of the standing wave, thus achieving resonance and amplifying the standing wave; and
   2) acquiring, by the vibration sensor, the standing wave amplified and determining whether to initiate an alarm.

7. The standing wave amplification device for vibration signal acquisition according to claim 5, wherein each of the two fixing support means comprises:
   a "U"-shaped fastener provided on an outer circumferential surface of the operating arm, and having two ends each provided with a thread;
   a fixing plate provided with two through holes through which the two ends of the "U"-shaped fastener pass respectively, wherein the fixing plate is connected with the "U"-shaped fastener by preload nuts engaged with the threads of the "U"-shaped fastener; and
   a clamp connected to the fixing plate, wherein the sensing rod is clamped inside the clamp, and a side wall of the clamp is provided with a threaded hole through which a bolt abuts against the sensing rod.

8. A ladle slag vibration signal detection method based on the standing wave amplification device for vibration signal acquisition according to claim 7, comprising:
   1) acquiring vibration waves at any two points on the operating arm by the two fixing support means, and superimposing, on the sensing rod, the vibration waves at the any two points so as to form a standing wave, wherein a vibration frequency of molten steel in a ladle shroud becomes the same as a frequency of the standing wave, thus achieving resonance and amplifying the standing wave; and
   2) acquiring, by the vibration sensor, the standing wave amplified and determining whether to initiate an alarm.

9. The standing wave amplification device for vibration signal acquisition according to claim 7, wherein an outer circumferential surface of the sensing rod is marked with scales.

10. A ladle slag vibration signal detection method based on the standing wave amplification device for vibration signal acquisition according to claim 9, comprising:
   1) acquiring vibration waves at any two points on the operating arm by the two fixing support means, and superimposing, on the sensing rod, the vibration waves at the any two points so as to form a standing wave, wherein a vibration frequency of molten steel in a ladle shroud becomes the same as a frequency of the standing wave, thus achieving resonance and amplifying the standing wave; and
   2) acquiring, by the vibration sensor, the standing wave amplified and determining whether to initiate an alarm.

11. The standing wave amplification device for vibration signal acquisition according to claim 9, wherein the vibration sensor is connected to the sensing rod by a fixing seat.

12. A ladle slag vibration signal detection method based on the standing wave amplification device for vibration signal acquisition according to claim 11, comprising:
   1) acquiring vibration waves at any two points on the operating arm by the two fixing support means, and superimposing, on the sensing rod, the vibration waves at the any two points so as to form a standing wave, wherein a vibration frequency of molten steel in a ladle shroud becomes the same as a frequency of the standing wave, thus achieving resonance and amplifying the standing wave; and
   2) acquiring, by the vibration sensor, the standing wave amplified and determining whether to initiate an alarm.

13. The standing wave amplification device for vibration signal acquisition according to claim 11, wherein the fixing seat comprises a base and a fixing member configured to fix the base to the sensing rod, the vibration sensor is connected to the base.

14. A ladle slag vibration signal detection method based on the standing wave amplification device for vibration signal acquisition according to claim 13, comprising:

1) acquiring vibration waves at any two points on the operating arm by the two fixing support means, and superimposing, on the sensing rod, the vibration waves at the any two points so as to form a standing wave, wherein a vibration frequency of molten steel in a ladle shroud becomes the same as a frequency of the standing wave, thus achieving resonance and amplifying the standing wave; and 2) acquiring, by the vibration sensor, the standing wave amplified and determining whether to initiate an alarm.

15. The standing wave amplification device for vibration signal acquisition according to claim 13, wherein the vibration sensor is mounted in a shielding protection box connected to the base by socket-head cap screws.

16. A ladle slag vibration signal detection method based on the standing wave amplification device for vibration signal acquisition according to claim 15, comprising:
1) acquiring vibration waves at any two points on the operating arm by the two fixing support means, and superimposing, on the sensing rod, the vibration waves at the any two points so as to form a standing wave, wherein a vibration frequency of molten steel in a ladle shroud becomes the same as a frequency of the standing wave, thus achieving resonance and amplifying the standing wave; and 2) acquiring, by the vibration sensor, the standing wave amplified and determining whether to initiate an alarm.

* * * * *